United States Patent
Arnold

(10) Patent No.: US 9,428,747 B2
(45) Date of Patent: Aug. 30, 2016

(54) METHODS FOR AMPLIFICATION OF NUCLEIC ACIDS UTILIZING HAIRPIN LOOP OR DUPLEX PRIMERS

(71) Applicant: Lyle J. Arnold, Poway, CA (US)

(72) Inventor: Lyle J. Arnold, Poway, CA (US)

( * ) Notice: Subject to any disclaimer, the term of this patent is extended or adjusted under 35 U.S.C. 154(b) by 36 days.

(21) Appl. No.: 14/214,621

(22) Filed: Mar. 14, 2014

(65) Prior Publication Data

US 2014/0274810 A1 Sep. 18, 2014

Related U.S. Application Data

(60) Provisional application No. 61/799,936, filed on Mar. 15, 2013.

(51) Int. Cl.
*C12P 19/34* (2006.01)
*C12N 15/10* (2006.01)
*C12Q 1/68* (2006.01)

(52) U.S. Cl.
CPC ......... *C12N 15/1065* (2013.01); *C12Q 1/6853* (2013.01)

(58) Field of Classification Search
CPC .......... C12Q 1/6853; C12Q 2521/501; C12Q 2525/301; C12Q 2563/185; C12N 15/1065
USPC ........................................................ 435/91.2
See application file for complete search history.

(56) References Cited

U.S. PATENT DOCUMENTS 8,071,311 B2 * 12/2011 Kurn .................... C12Q 1/6853
435/6.12
2013/0203123 A1 * 8/2013 Nelson ................. C12Q 1/6811
435/91.52
2015/0205914 A1 * 7/2015 Richards .............. C12Q 1/6874
506/2

* cited by examiner

*Primary Examiner* — Cynthia B Wilder
(74) *Attorney, Agent, or Firm* — David B. Waller

(57) ABSTRACT

The present invention provides methods of amplifying a target nucleic acid utilizing duplex primer. The first strand of the primer comprises a random nucleotide sequence of about 6 to about 9 nucleotides in length that is able to hybridize to the target nucleic acid and a tag sequence. The second strand of the primer comprises a sequence complementary to the tag sequence allowing the primer to form a duplex and the ability to bind the tag sequence of the product nucleic acid for further amplification. The resulting nucleic acid produced contains tag sequences on both the 3'- and 5'-termini.

3 Claims, 1 Drawing Sheet

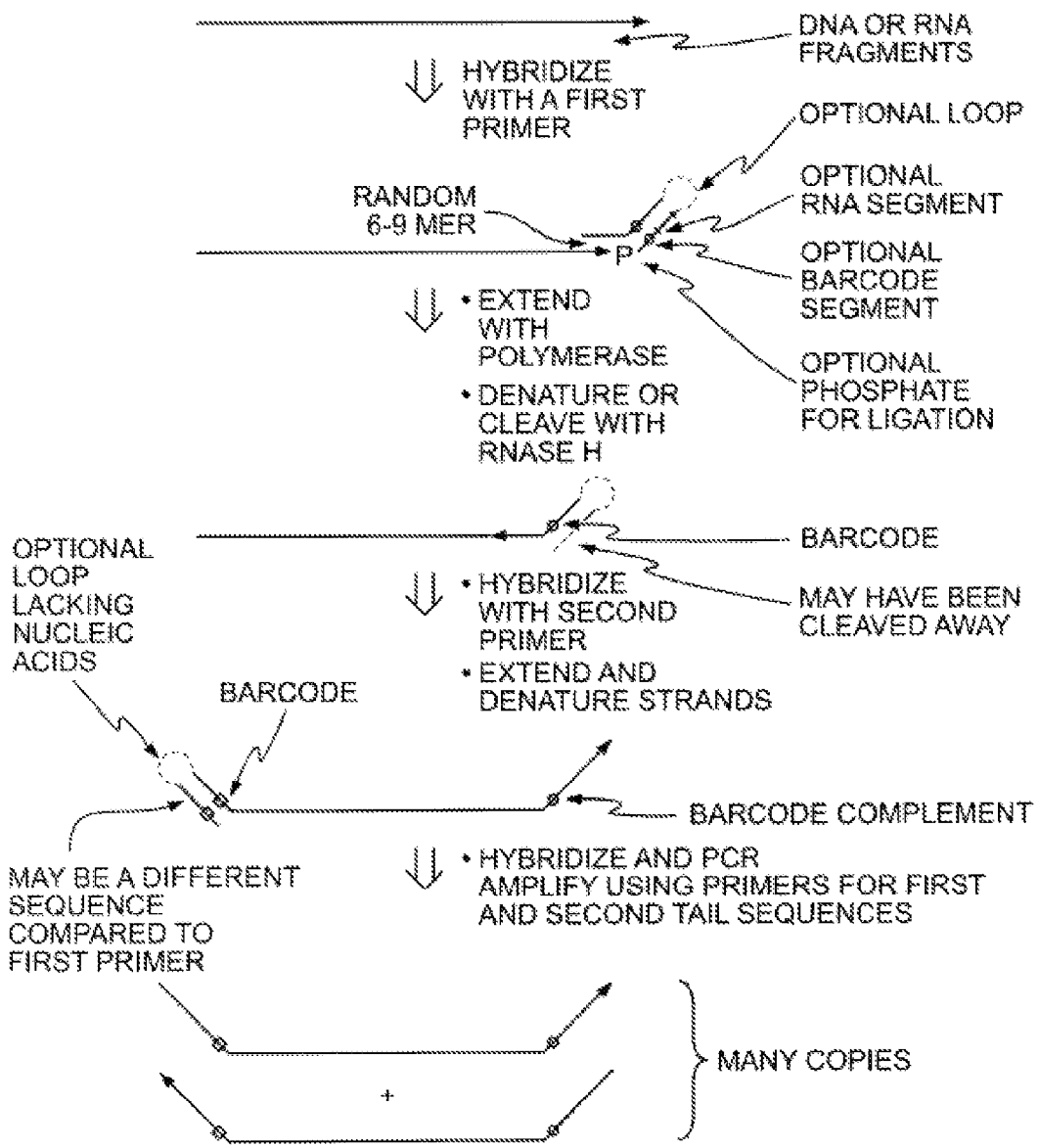

METHODS FOR AMPLIFICATION OF NUCLEIC ACIDS UTILIZING HAIRPIN LOOP OR DUPLEX PRIMERS

CROSS-REFERENCE TO RELATED APPLICATIONS

This application is a non-provisional patent application of provisional patent application Ser. No. 61/799,936 filed Mar. 15, 2013 incorporated herein in its entirety.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION (1) Field of the Invention

The present invention relates to methods of amplification of nucleic acids. Specifically, nucleic acid amplification using duplex primers.

(2) Description of Related Art

There are a variety of methods for the amplification of nucleic acids known to those skilled in the art. Providing unique tail sequences during the amplification process can be useful for capturing, detecting or sequencing a target nucleic acid and eliminate the need to perform additional steps after amplification if labeling the target nucleic acid is desired. Furthermore, methods in the art that utilize random primers to assure good coverage of a number of target sequences in a sample also suffer from the problem that they can bind in a wide variety of locations on the target or target fragments, generating a wide range of amplicon sizes. The method disclosed in the present invention solves this problem by directing annealing of the random primers with tags more favorably to the ends of the target molecules and fragments thereof, as well as cDNA strands generated from these target molecules and fragments, thus generating longer and more uniform in size amplicons with tags incorporated at both ends. In addition, amplification methods often involve multiple steps. Reducing the number of steps required can save time and resources. The present invention provides a method for incorporating unique tail sequences during amplification as well as a duplex primer having a first strand for binding and expanding the target nucleic acid while the second strand may be used to expand the product.

BRIEF SUMMARY OF THE INVENTION

The present invention provides methods of amplifying a target nucleic acid. In one method, amplification begins by mixing a duplex primer with a target nucleic acid. The duplex primer is a two stranded oligonucleotide complex. The first strand comprises a target-binding region on its 3'-terminus comprising a random nucleotide sequence of about 6 to about 9 nucleotides in length and tag sequence on its 5'-terminus. The second strand comprises a sequence complementary to at least a portion of the 3'-terminus of the tag sequence, thus allowing the first and second strands to form a duplex with at least a portion of the tag region.

The random nucleotide sequence of the duplex primer is annealed to the target nucleic acid. This occurs primarily at the 3'-terminus of the target nucleic acid, which is favored due to base stacking between the 3'-terminus of the target nucleic acid and the 5'-terminus of the second strand of the duplex primer. In an optional mode, the second strand of the duplex primer can be ligated to the 3' terminus of the target sequence. In this mode, the second strand of the duplex strand contains a 5'-phosphate in order to effectuate ligation. A polymerase enzyme is utilized to extend the primer and produce a first duplex nucleic acid containing a first nucleic acid and the target nucleic acid. This first nucleic acid contains a double stranded tag on the 5'-terminus. The first nucleic acid is then removed from the target nucleic acid. In an alternative mode, a ribonucleotide segment within the second strand of the duplex primer may be cleaved to render it ineffective in subsequent ligation reactions. Heat denaturation may be used to separate the strands. Alternatively, when the target is RNA, the target may be cleaved using RNaseH. However the duplex tag region may be denatured as well. Consequently, this strand is reannealed to the primer and the primer is hybridized to the first nucleic acid. In another embodiment, when the two strands of the tag region are connected by a loop, the strands will denature but rapidly reanneal when the denaturing conditions are removed.

A second duplex primer is then annealed to the first nucleic acid, preferably to the 3'-terminus of the first nucleic acid, and extended utilizing polymerase to produce a second duplex that contains the first nucleic acid and a second nucleic acid. The second nucleic acid contains tag sequences on both the 3'- and 5'-termini. In some modes, the tags on the 3'- and 5'-termini may be complementary to each other. The second nucleic acid is removed from the first nucleic acid and may now undergo further manipulation, including isolation, purification, detection, sequencing and/or amplification utilizing an oligonucleotide complementary to a portion of the tag sequence.

In one embodiment of the present invention, the duplex primer is a provided in a hairpin configuration. The hairpin primer is a single oligonucleotide strand that comprises a target-binding region comprising a random nucleotide sequence of about 6 to about 9 nucleotides in length on its 3'-terminus and a tag sequence on its 5'-terminus. The 5'- and 3'-termini of the tag sequence are complementary and are separated by an intervening non-complementary segment. The tag sequence thus forms a hairpin structure, with the complementary segments forming a double stranded stem and the non-complementary segment forming a loop.

In other aspects of the invention, said random nucleotide sequence is selected from bases that are pseudo-complementary, in that they hybridize with much greater avidity to natural nucleic acid bases than they do to each other. This mode helps reduce possible primer-dimer interactions. Such bases include 2-thiothymine, 2-aminoadenine, 5-methylcytosine, 7-methyldeazaquanine, 6-thioguanine, 7-ethyl-7-deazaguanine, $N^4$-ethylcytosine. (See Nuc. Acid. Res. 2008, 36, 6999-7008 and references contained therein.)

Other aspects of the invention are found throughout the specification.

BRIEF DESCRIPTION OF THE DRAWINGS

FIG. 1 is a schematic diagram of one method of the present invention.

DETAILED DESCRIPTION OF THE INVENTION

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "oligonucleotide" as used herein refers to a polymeric form of nucleotides, either ribonucleotides or deoxyribonucleotides, incorporating natural and non-natural nucleotides of a length ranging from at least 2, or generally about 5 to about 200, or more commonly to about 100. Thus, this term includes double- and single-stranded DNA and RNA. In addition, oligonucleotides may be nuclease resistant and include but are not limited to 2'-O-methyl ribonucleotides, phosphorothioate nucleotides, phosphorodithioate nucleotides, phosphoramidate nucleotides, and methylphosphonate nucleotides.

The terms "tag region" or "tag sequence" refer to a user-defined nucleic acid sequence or sequences that are incorporated into an oligonucleotide or other nucleic acid structure, such as a primer, to provide one or more desired functionalities. Examples of such elements include, for example, adapters, sequencing primers, amplification primers, capture and/or anchor elements, hybridization sites, promoter elements, restriction endonuclease site, detection elements, mass tags, barcodes, binding elements, and/or non-natural nucleotides. Other elements include those that clearly differentiate and/or identify one or more nucleic acids or nucleic acid fragments in which a tag sequence has been incorporated from other nucleic acids or nucleic acid fragments in a mixture, elements that are unique in a mixture of nucleic acids so as to minimize cross reactivity and the like and elements to aid in the determination of sequence orientation. Some or all of the elements in a tag sequence can be incorporated into amplification products.

The term "target," "target sequence," or "target nucleic acid" as used herein refers to a nucleic acid that contains a polynucleotide sequence of interest, for which purification, isolation, capture, immobilization, amplification, identification, detection, quantitation, mass determination and/or sequencing, and the like is/are desired. The target sequence may be known or not known, in terms of its actual sequence.

The term "primer" or "primer sequence" as used herein are nucleic acids comprising sequences selected to be substantially complementary to each specific sequence to be amplified. More specifically, primers are sufficiently complementary to hybridize to their respective targets. Therefore, the primer sequence need not reflect the exact sequence of the target. Non-complementary bases or longer sequences can be interspersed into the primer, provided that the primer sequence has sufficient complementarity with the sequence of the target nucleic acid to permit hybridization and extension. Furthermore, random or semi-random sequences may be utilized to hybridize with a much broader range of nucleic acid targets in a sample. This may be desired for applications including but not limited to whole genome or whole transcriptome amplification, whole exome amplification, amplification of specific genes or gene regions and amplification of groups of bacteria or viruses.

In addition, primers may be nuclease resistant and include primers that have been modified to prevent degradation by exonucleases. In some embodiments, the primers have been modified to protect against 3' or 5' exonuclease activity. Such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the primer(s) and/or probe(s) employed in an amplification reaction are protected against 3' and/or 5' exonuclease activity by one or more modifications.

The skilled artisan is capable of designing and preparing primers that are appropriate for extension of a target sequence. The length of primers for use in the methods and compositions provided herein depends on several factors including the nucleotide sequence identity and the temperature at which these nucleic acids are hybridized or used during in vitro nucleic acid extension. The considerations necessary to determine a preferred length for the primer of a particular sequence identity are well known to the person of ordinary skill.

The term "hybridization," "hybridize," "anneal" or "annealing" as used herein refers to the ability, under the appropriate conditions, for nucleic acids having substantial complementary sequences to bind to one another by Watson & Crick base pairing. Nucleic acid annealing or hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994). The term "substantial complementary" as used herein refers both to complete complementarity of binding nucleic acids, in some cases referred to as an identical sequence, as well as complementarity sufficient to achieve the desired binding of nucleic acids. Correspondingly, the term "complementary hybrids" encompasses substantially complementary hybrids.

As used herein, the term "complementary," in the context of an oligonucleotide (i.e., a sequence of nucleotides such as an oligonucleotide primers or a target nucleic acid) refers to standard Watson/Crick base pairing rules. For example, the sequence "5'-A-G-T-C-3'" is complementary to the sequence "3'-T-C-A-G-5'." Certain nucleotides not commonly found in natural nucleic acids or chemically synthesized may be included in the nucleic acids described herein; these include but not limited to base and sugar modified nucleosides, nucleotides, and nucleic acids, such as inosine, isocytosine and isoguanine. Complementarity need not be perfect; stable duplexes may contain mismatched base pairs, degenerative, or unmatched nucleotides. Those skilled in the art of nucleic acid technology can determine duplex stability empirically considering a number of variables including, for example, the length of the oligonucleotide, base composition and sequence of the oligonucleotide, incidence of mismatched base pairs, ionic strength, other hybridization buffer components and conditions.

Complementarity may be partial in which only some of the nucleotide bases of two nucleic acid strands are matched according to the base pairing rules. Complementarity may be complete or total where all of the nucleotide bases of two nucleic acid strands are matched according to the base pairing rules. Complementarity may be absent where none of the nucleotide bases of two nucleic acid strands are matched according to the base pairing rules. The degree of complementarity between nucleic acid strands has significant effects on the efficiency and strength of hybridization between nucleic acid strands. This is of particular importance in ligation and amplification reactions, as well as detection methods that depend upon binding between nucleic acids.

The term "sample" as used herein refers to essentially any sample containing the desired target nucleic acid(s), including but not limited to tissue or fluid isolated from a human being or an animal, including but not limited to, for example, blood, plasma, serum, spinal fluid, lymph fluid, tears or saliva, urine, semen, stool, sputum, vomit, stomach aspirates, bronchial aspirates, swabs (nasopharyngeal, rectal, ocular, urogenital, etc.), organs, muscle, bone marrow, FFPE tissue, skin, tumors and/or cells obtained from any part of the organism; plant material, cells, fluid, etc.; an individual bacterium, groups of bacteria and cultures thereof; food; cosmetics; drugs/pharmaceuticals; materials prepared via bioprocessing (finished product as well as intermediate materials); water; environmental samples, including but not limited to, for example, soil, water and air; semi-purified or purified nucleic acids from the sources listed above, for example; nucleic acids that are the result of a process, such as template formation for sequencing, including next generation sequencing, sample processing, nuclease digestion, restriction enzyme digestion, replication, and the like.

The term "amplification," "amplifying" or "amplified" as used herein refers to the process of creating nucleic acid strands that are identical or complementary to a complete target nucleic acid sequence, or a portion thereof, or a universal sequence that serves as a surrogate for the target nucleic acid sequence. The term "identical" as used herein refers to a nucleic acid having the same or substantially the same nucleotide sequence as another nucleic acid.

The term "nucleic acid" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions.

Nitrogenous bases may be conventional bases (A, G, C, T, U), non-natural nucleotides such as isocytosine and isoguanine, analogs thereof (e.g., inosine; The Biochemistry of the Nucleic Acids 5-36, Adams et al., ed., 11th ed., 1992), derivatives of purine or pyrimidine bases (e.g., $N^4$-methyl deoxyguanosine, deaza- or aza-purines, deaza- or aza-pyrimidines, pyrimidines or purines with altered or replacement substituent groups at any of a variety of chemical positions, e.g., 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121).

Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, Biochemistry 43(42):13233-41).

The term "releasing" or "released" as used herein refers to separating one nucleic acid from its complementary nucleic acid. For example, separating the desired amplified nucleic acid from its template or separating duplex primer stands from one another. This can be achieved by heating the duplex to a temperature that denatures the nucleic acid duplex forming two separate oligonucleotide strands.

The term "removing" as used herein refers to a variety of methods used to isolate or otherwise remove one nucleic acid strand of a duplex from another, such as for example enzymatic, thermal and/or chemical digestion, degradation and/or cleavage of one of the strands of the duplex, or denaturation/dissociation of the strands by heat, acoustic energy, chemicals, enzymes or a combination thereof.

General methods for amplifying nucleic acid sequences have been well described and are well known in the art. Any such methods can be employed with the methods of the present invention. In some embodiments, the amplification uses digital PCR methods, such as those described, for example, in Vogelstein and Kinzler ("Digital PCR," *PNAS*, 96:9236-9241 (1999); incorporated by reference herein in its entirety). Such methods include diluting the sample containing the target region prior to amplification of the target region. Dilution can include dilution into conventional plates, multiwell plates, nanowells, as well as dilution onto micropads or as microdroplets. (See, e.g., Beer N R, et al., "On-chip, real time, single copy polymerase chain reaction in picoliter droplets," *Anal. Chem.* 79(22):8471-8475 (2007); Vogelstein and Kinzler, "Digital PCR," *PNAS*, 96:9236-9241 (1999); and Pohl and Shih, "Principle and applications of digital PCR," *Expert Review of Molecular Diagnostics*, 4(1):41-47 (2004); all of which are incorporated by reference herein in their entirety.) In some embodiments, the amplification is by digital PCR.

In some cases, the enzymes employed with the methods of the present invention for amplification of the target region include but are not limited to high-fidelity DNA polymerases, for example DNA polymerases that have 3'-5' exonuclease proof-reading capabilities. Examples of enzymes that can be used with the methods include but are not limited to AmpliTaq, Phusion HS II, Deep Vent, and Kapa HiFi DNA polymerase.

High-fidelity enzymes allow for high-fidelity (highly accurate) amplification of a target sequence. In some embodiments, the enzymes employed will include high-fidelity DNA polymerases, for example DNA polymerases that have 3'-5' exonuclease proofreading capabilities. Enzymes that can be used with the methods include but are not limited to AmpliTaq, Phusion HS II, Deep Vent, and Kapa HiFi DNA polymerase.

The amplification product can be detected/analyzed using a number of methods known to those skilled in the art including, but not limited to, fluorescence, electrochemical detection, gel analysis and sequencing. Furthermore, the product can be quantitated using a number of methods known to those skilled in the art such as real time amplification. Quantitation can be normalized by comparison to so-called "house-keeping genes" such as actin or GAPDH or to an internal control that can be added to the reaction in a known amount. Such methods are well known and have been described in Sambrook and Russell, *Molecular Cloning: A Laboratory Manual* (3rd Ed.) (2001).

Instrumentation for performing the methods described herein is readily available. Such instruments can include instruments for real-time and end-point PCR assays, emulsion PCR, solid-phase PCR, melting curve analyses, and sequencing analyses. Such instruments include Life Technologies 7500 Fast Dx real-time instrument (which is also capable of high-resolution melting curve analyses) and the 3500xl capillary gel instruments. Other instruments known in the art to be useful in the methods of the present invention are also contemplated for use by one of skill in the art in practicing the methods of the present invention.

The present invention is a method for introducing selected tag sequences during amplification of a target nucleic acid utilizing a duplex primer (FIG. 1). In one embodiment, the duplex primer is two stranded oligonucleotide complex. The first strand comprises a target-binding region on its 3-terminus comprising a random nucleotide sequence of about 6 to about 9 nucleotides in length and a unique tag sequence on its 5'-terminus. The second strand comprises a sequence complementary to at least a 3' portion of the tag sequence, thus allowing the first and second strands to form a duplex with at least a portion of the tag region.

In the methods of the present invention, the duplex primer is mixed or contacted with a sheared or otherwise fragmented nucleic acid target. The target may be DNA or RNA nucleic acid. The target-binding region of the duplex primer is annealed or binds the fragments of the target nucleic acid. This binding is preferentially to the 3'-end of the target nucleic acid due to the extra stability afforded the primer/target duplex through base stacking between the 3'-terminus of the target nucleic acid and the 5'-terminus of the second strand. This base stacking is not available when the primer binds at any other location of the target. The 3'-terminus of the target-binding region of the duplex primer is extended using a polymerase enzyme to produce a first duplex nucleic acid containing a first nucleic acid and the target nucleic acid. In this example, the first nucleic acid is a cDNA strand for each of the target nucleic acid fragments.

The first nucleic acid is removed from the target nucleic acid. This may be performed by a variety of methods such as RNaseH digestion if the target nucleic acid is RNA or by heat denaturation if the target is DNA. If heat denaturation is used, removed duplex primer strands will reanneal when the temperature is lowered. Following removal the duplex primer is annealed to the first nucleic acids in a manner analogous to its original binding the target fragments. Preferably the duplex primer hybridizes at the 3'-terminus of the first nucleic acids. The 3'-end of the target-binding region of the duplex primer is extended using a polymerase enzyme to produce a second nucleic acid duplex containing a second nucleic acid and the first nucleic acid. In this example the second nucleic acid is a cDNA strand for each of the first nucleic acids, having user-defined sequences on both ends.

The second nucleic acid is removed from the first nucleic acid. This second nucleic acid can be further manipulated, such as for example amplification using PCR with a primer complementary to a portion of the tag sequence.

In another embodiment, the duplex primer is provided in a hairpin configuration. The hairpin primer is a single oligonucleotide strand that comprises a target binding region comprising a random nucleotide sequence of about 6 to about 9 nucleotides in length on its 3'-terminus and a tag sequence on its 5'-terminus. The 5'- and 3'-termini of the tag sequence are complementary and are separated by an intervening non-complementary segment. The tag sequence thus forms a hairpin structure, with the complementary segments forming a double stranded stem and the non-complementary segment forming a loop. In one aspect of this embodiment, the hairpin primer is ligated to the second nucleic acid duplex at both ends forming a circular nucleic acid. This circular nucleic acid may be further utilized in a number of applications, including sequencing and particularly next generation sequencing.

The information set forth above is provided to give those of ordinary skill in the art a complete disclosure and description of how to make and use the embodiments of the device and methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference. For example, many of the wash steps cited in the different methods are optional as are some of the steps that remove and/or separate two nucleic acid strands from one another. Not performing at least some of the wash and/or separation steps will afford a faster, simpler and more economical work flow, while still achieving the desired results. In another example, the stepwise addition/binding of certain oligonucleotides and/or target nucleic acids in the exemplified methods may be combined. Furthermore, a variety of polymerases, extension conditions and other amplification protocols known to those skilled in the art may be used in various steps or combination of steps in the methods described above. Other obvious modifications to the methods disclosed that would be obvious to those skilled in the art are also encompassed by this invention.

What is claimed is:

1. A method of amplifying a target nucleic acid, said method comprising the steps of:
   A. annealing a first duplex primer to a target nucleic acid in a mixture comprising said first duplex primer and said target nucleic acid wherein said first duplex primer comprises a first strand and a second strand, wherein said first strand having a random nucleotide sequence of about 6 to about 9 nucleotides in length on the 3'-terminus and a first tag sequence on its 5'-terminus and said second strand having a sequence substantially complementary to a portion of said tag sequence of said first strand, extending said duplex primer by a polymerase to produce a first duplex nucleic acid containing a first nucleic acid having a double stranded tag sequence and target nucleic acid, and optionally removing said first nucleic acid from said target nucleic acid;
   B. annealing a second duplex primer to said first nucleic acid wherein said second duplex primer comprises a third strand and a fourth strand, wherein said third strand having a random nucleotide sequence of about 6 to about 9 nucleotides in length on the 3'-terminus and a second tag sequence on its 5'-terminus and said fourth strand having a sequence substantially complementary to a portion of said tag sequence of said third strand, extending said duplex primer by a polymerase to produce a second duplex containing said first nucleic acid and said second nucleic acid having a second tag sequence on the 5'-terminus and the complement to the first tag sequence on the 3'-terminus, and optionally removing said second nucleic acid from said first nucleic acid;
   C. annealing a first single stranded primer to said second nucleic acid wherein said first single stranded primer comprises a sequence substantially the same as said first tag sequence, extending said first single stranded primer by a polymerase to produce a third nucleic acid duplex containing said second nucleic acid and a third nucleic acid having said first tag sequence on the 5'-terminus and the complement to said second tag sequence on the 3'-terminus, removing said second nucleic acid from the third nucleic acid, annealing the said first single stranded primer to said second nucleic acid and a second single stranded primer to the third nucleic acid wherein said second single stranded primer comprises a sequence substantially the same as said second tag, extending said first and second single stranded primer to create additional copies of said second and said third nucleic acids, optionally removing the second nucleic acid from the third nucleic acid and repeating this cycle of annealing and extending the first and second primers and optionally removing the second strand from the third strand to further amplify said target nucleic acid.

2. The method according to claim 1, wherein said first and said second tag sequences have the same sequence.

3. The method adding to claim 1, wherein said first and second single stranded primers optionally contain tag sequences.

\* \* \* \* \*